(12) United States Patent
Carney et al.

(10) Patent No.: US 7,955,824 B2
(45) Date of Patent: Jun. 7, 2011

(54) METHODS OF MAKING EPOTHILONES

(75) Inventors: John R. Carney, Hayward, CA (US); Yong Li, Hayward, CA (US); Hugo Menzella, Hayward, CA (US); Ralph C. Reid, Hayward, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 604 days.

(21) Appl. No.: 12/118,432

(22) Filed: May 9, 2008

(65) Prior Publication Data
US 2009/0076289 A1    Mar. 19, 2009

Related U.S. Application Data

(60) Provisional application No. 60/917,452, filed on May 11, 2007, provisional application No. 60/917,572, filed on May 11, 2007.

(51) Int. Cl.
*C12P 17/06* (2006.01)

(52) U.S. Cl. ........ 435/125; 549/292; 549/417; 558/250; 558/254

(58) Field of Classification Search .................. 435/125; 549/292, 417; 558/254, 250
See application file for complete search history.

(56) References Cited

U.S. PATENT DOCUMENTS

2009/0149516 A1 *  6/2009  Danishefsky et al. ........ 514/365

FOREIGN PATENT DOCUMENTS

WO         200212534        2/2002

* cited by examiner

*Primary Examiner* — Bernard Dentz
*Assistant Examiner* — David E Gallis
(74) *Attorney, Agent, or Firm* — Hong Liu

(57) ABSTRACT

The invention provides novel compounds that may be used as intermediates in the preparation of epothilones, epothilone analogs and derivative, as well as new synthetic methods for producing the intermediates and products.

19 Claims, 5 Drawing Sheets

METHODS OF MAKING EPOTHILONES

CROSS-REFERENCE TO RELATED APPLICATIONS

This application claims benefit of U.S. provisional application No. 60/917,452, filed May 11, 2007, and of U.S. provisional application No. 60/917,572, filed May 11, 2007, the entire contents of which are incorporated herein by reference for all purposes.

STATEMENT AS TO RIGHTS TO INVENTIONS MADE UNDER FEDERALLY SPONSORED RESEARCH AND DEVELOPMENT

Work described in this application has been supported, in part, by National Institute of Standards and Technology grant number 2002004678. The U.S. government has certain rights in the invention.

FIELD OF THE INVENTION

The present invention relates to compounds useful in the synthesis of epothilones and methods for producing the compounds.

BACKGROUND OF THE INVENTION

The class of polyketides known as epothilones has emerged as a source of therapeutic compounds having modes of action similar to paclitaxel. Interest in the epothilones and epothilone analogs has grown with the observations that certain epothilones are active against tumors that have developed resistance to paclitaxel, and have reduced potential for undesirable side-effects. Among the epothilones and epothilone analogs being investigated for therapeutic efficacy are the natural product epothilone B, the semi-synthetic epothilone B derivative BMS-247550, also known as ixabepilone, and the synthetic analog EPO-ZK.

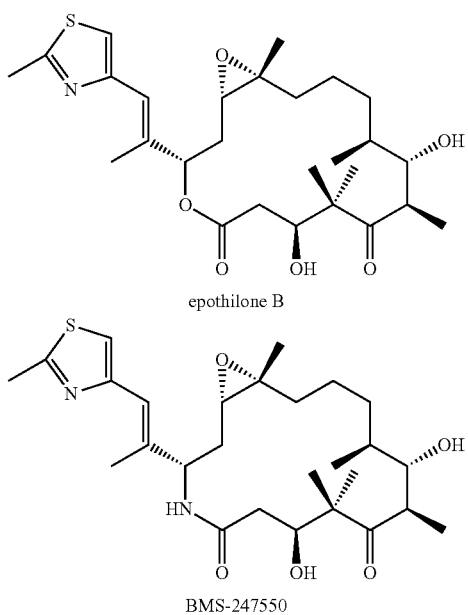

epothilone B

BMS-247550

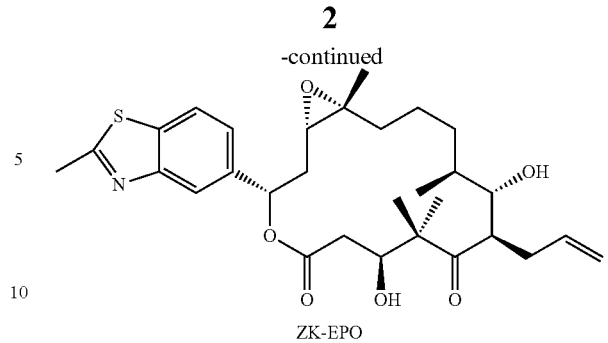

ZK-EPO

Desoxyepothilone B, also known as "epothilone D" is another epothilone derivative having promising anti-tumor properties that is being investigated for therapeutic efficacy. This compound has demonstrated lower toxicity than epothilones having 12,13-epoxides.

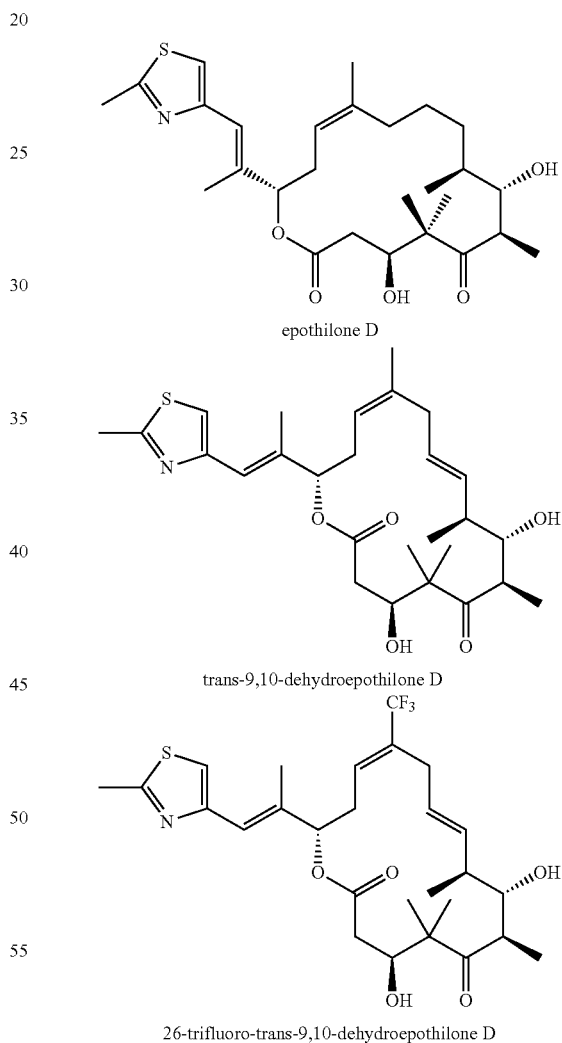

epothilone D trans-9,10-dehydroepothilone D 26-trifluoro-trans-9,10-dehydroepothilone D More recently analogs of epothilone D having greater in vitro potency have been described, including trans-9,10-dehydroepothilone D ((4S, 7R, 8S,9S, 10E, 13Z, 16S)-4,8-dihydroxy-5,5,7,9,13-pentamethyl-16-[(1E)-1-methyl-2-(2-methyl-4-thiazolyl)ethenyl]-oxacyclohexadeca-10,13-diene-2,6-dione) and its 26-trifluoro-analog, also known as fludelone. These compounds demonstrate remarkable antitumor activity in mouse xenograft models (Rivkin et al., "Discovery of (E)-9,10-dehydroepothilones through Chemical Synthesis: On the Emergence of 26-Trifluoro-(E)-9,10-dehydro-12,13-desoxyepothilone B as a Promising Anticancer Drug Candidate," *J. Am. Chem. Soc.* 126: 10913-10922 (2004)).

Although various methods for preparing epothilone derivatives and analogs having anti-tumor activity have been disclosed in the art, including fermentation, semi-synthesis, and total chemical synthesis, there is continuing unmet need for new, more efficient methods for preparing these promising anticancer agents.

SUMMARY OF THE INVENTION

The present invention provides new methods and compounds for the preparation of epothilones and epothilone derivatives and analogs, hereafter collectively referred to as "epothilones." According to the invention, epothilones may be prepared using a combination of chemical synthetic and biosynthetic steps. In one aspect, methods are provided in which one or more intermediates used for epothilone synthesis are obtained through fermentation of recombinant cells. The methods and compounds provided by the invention have the potential to greatly reduce the cost of manufacture of epothilones, thus facilitating their commercial development as therapeutic agents.

In one aspect, compounds useful in the preparation of epothilones are provided, having the following formula (II):

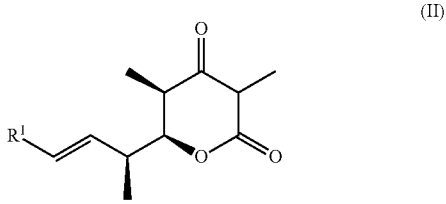

(II)

wherein $R^1$ is H, unsubstituted lower alkyl, or substituted lower alkyl. In a particular embodiment, compounds of formula (II) wherein $R^1$ is H or unsubstituted lower alkyl are provided.

In another aspect, the present invention provides methods for preparing compounds of formula (II). In certain embodiments, the invention provides methods for preparing compounds of formula (II) through the fermentation. In particular embodiments, the invention provides methods for preparing compounds of formula (II) through fermentation of engineered organisms.

In one embodiment, compounds having formula (II) are prepared using fermentation of host cells comprising polyketide synthases. In one particular embodiment, compounds having formula (II) are prepared using fermentation of host cells comprising polyketide synthases capable of converting compounds of the formula (I)

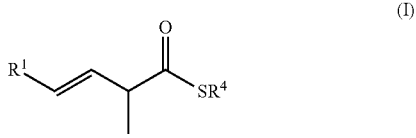

(I)

wherein $R^1$ is H, unsubstituted lower alkyl, or substituted lower alkyl; and $R^4$ is $C_1$-$C_{10}$ alkyl; or $R^4$ is $CH_2CO_2R^6$, wherein $R^6$ is lower alkyl; or $R^4$ is $CH_2CH_2NH(CO)R^5$, wherein $R^5$ is $C_1$-$C_{10}$ alkyl; into compounds having formula (II). In certain embodiments, the invention provides methods for preparation of compounds of formula (II) using fermentation of host cells comprising polyketide synthases capable of converting compounds of the formula (I) wherein $R^4$ is $CH_2CH_2NH(CO)R^5$ into compounds of formula (II). In particular embodiments, the invention provides methods for preparation of compounds of formula (II) using fermentation of host cells comprising polyketide synthases capable of converting compounds of the formula (I) wherein $R^4$ is $CH_2CH_2NHC(=O)CH_3$ into compounds of formula (II). These and many other aspects of the invention are described hereinbelow.

DETAILED DESRIPTION OF THE INVENTION

Definitions

Figure 1:
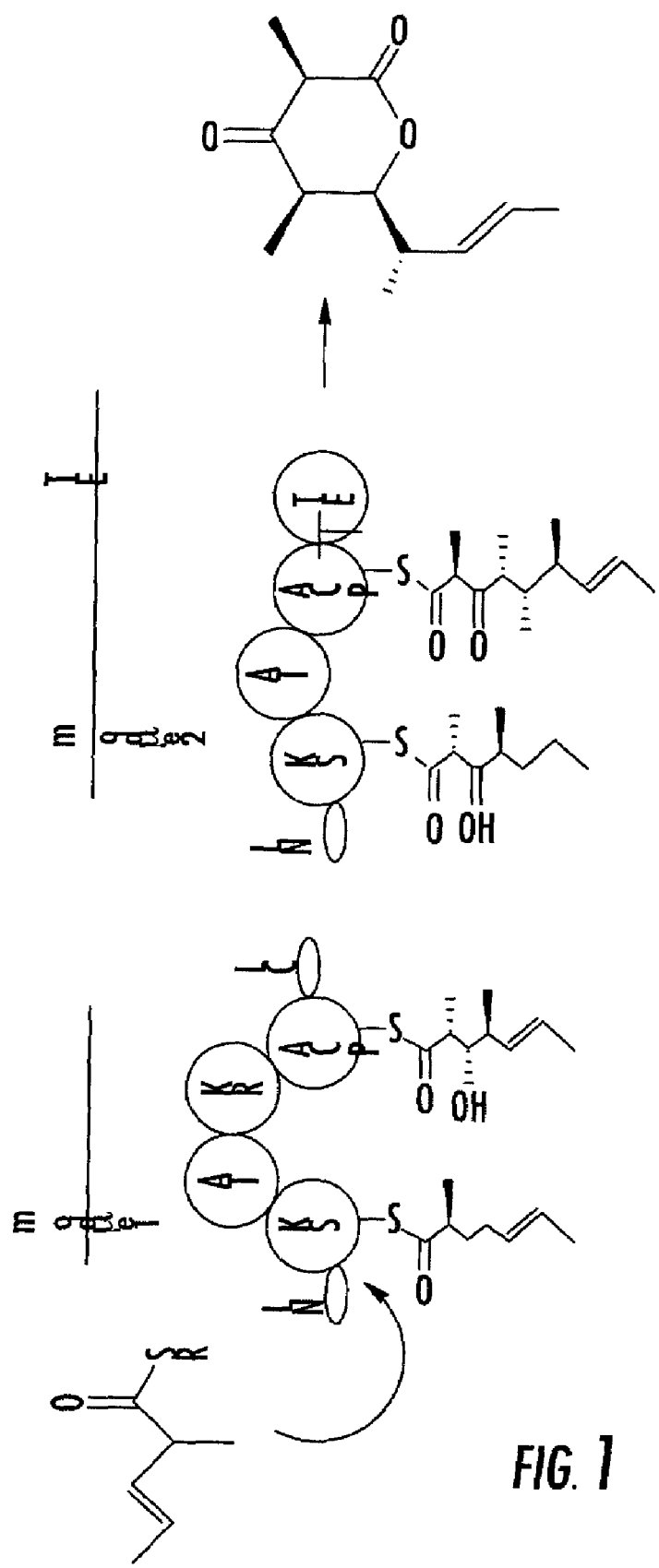
FIG. 1 illustrates one embodiment of the invention, in which a compound of formula I is biosynthetically converted to a compound of formula (II) using a two-module polyketide synthase. Specifically, a 2-methyl-3-pentenoate thioester is converted to (5R,6S)-3,3,5-trimethyl-6-((S,E)-pent-3-en-2-yl)-dihydro-3H-pyran-2,4-dione (Compound 1).

As used herein, the term "alkyl" refers to a straight or branched, saturated aliphatic radical containing one to ten carbon atoms. Unless otherwise indicated alkyl includes methyl, ethyl, propyl, isopropyl, butyl, sec-butyl, isobutyl, tert-butyl, and the like. The term "lower alkyl" refers to an alkyl radical having from one to four carbon atom The term "aryl" refers to a monocyclic or fused bicyclic ring assembly containing 6 to 10 ring carbon atoms wherein each ring is aromatic e.g., phenyl or naphthyl.

The term "arylalkenyl" refers to a group —$R^xR^y$ wherein $R^y$ is an aryl group and $R^x$ is an alkenyl group wherein the alkenyl portions has from one to six carbon atoms and from one to three double bonds. Examples of arylalkenyl groups are styryl, 1-phenylpropen-2-yl, 3-phenyl-propen-1-yl, and the like.

The term "heteroaryl" refers to a monocyclic or fused bicyclic ring assembly containing 6 to 10 ring atoms wherein each ring is aromatic at least one of the ring atoms is a heteroatom (N, O, S). Examples of heteroaryl group are pyridyl, pyimidinyl, thienyl, furanyl, thiazolyl, pyrazolyl, oxazolyl, quinolinyl, quinazolinyl, benzofuranyl, benzothiazolyl, benzimidazolyl, and the like.

The term "heteroarylalkenyl" refers to a —$R^xR^y$ wherein $R^y$ is a hteroaryl group and $R^x$ is an alkenyl group wherein the alkenyl portions has from one to six carbon atoms and from one to three double bonds. Examples of heteroarylalkenyl groups are styryl, 1-(thiazol-2-yl)ethenyl, 2-(thiazol-2-yl)ethenyl, 2-(2-pyridyl)propen-1-yl, and the like.

The term "substituted" refers to the presense of an additional substituent group selected from halogen (preferably fluoro, chloro, or bromo), hydroxy, amino, mercapto, and the like. Preferred substituents for the groups described herein as substituted lower alkyl or substituted alkyl are halogens, particularly fluoro substituents.

As used herein, the term "chiral auxiliary" refers to a group that imparts directional influence to a particular reaction. In the present invention, a chiral auxiliary is used with an aldol condensation to provide a product having a preponderance of one stereochemistry over another stereochemistry. A review of chiral auxiliaries is provided in Evans, ASYMMETRIC SYNTHESIS—THE ESSENTIALS, Christmann and Brase, eds., Wiley-VCH 2007, pages 3-9.

The following abbreviations are used: acyltransferase (AT); acyl carrier protein (ACP); beta-ketoacylsynthase (KS); ketoreductase (KR); dehydratase (DH); enoylreductase (ER); thioesterase (TE); amino terminal interpolypeptide linker (LN); and carboxy-terminal interpolypeptide linker (LC); intrapolypeptide linker (LI).

Introduction

In one aspect, the present invention provides compounds useful in the preparation of epothilones. By "epothilones" is meant a compound of general structure

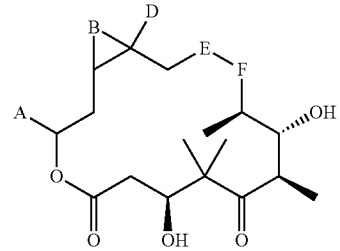

wherein A is aryl, heteroaryl, arylalkenyl, or heteroarylalkenyl, B is —O— or a bond, D is H or unsubstituted or substituted lower alkyl, and E-F is C=C, preferably trans, or $CH_2$—$CH_2$, and includes the naturally-occurring epothilones known in the art, for example those described in Hardt et al., "New Natural Epothilones from *Sorangium cellulosum*, Strains So ce90/B2 and So ce90/D13: Isolation, Structure Elucidation, and SAR Studies," *J. Natural Products* 64: 847-56 (2001), as well as synthetic derivatives and analogs thereof, for example epothilone analogs having a 9,10-alkene such as those described in Rivkin et al., "Discovery of (E)-9,10-dehydroepothilones through Chemical Synthesis: On the Emergence of 26-Trifluoro-(E)-9,10-dehydro-12,13-desoxyepothilone B as a Promising Anticancer Drug Candidate," *J. Am. Chem. Soc.* 126: 10913-10922 (2004), each of which is incorporated herein by reference.

Without intending to limit the invention, the methods described herein may be used in the production of synthesis of epothilones and other therapeutically valuable compounds. In one aspect, a compound of formula (I) (all compounds are described hereinbelow) is produced as described below. In one aspect, a compound of formula (I) is used in a biosynthetic step to produce a compound of formula (II). In one aspect a compound of formula (II) is used to produce epothilones and epothilone analogs (such as, for example and not limitation, Compound 14 shown in FIG. 5). Thus, in one embodiment the synthesis of epothilones according to an aspect of the invention is shown in the scheme below:

Starting Material→Compounds of formula I⇒Compounds of formula II→Epothilones & Analogs In this scheme, "⇒" represents biosynthetic steps and "→" represents chemical synthetic steps. Thus compounds of formula (I) and (II) are intermediates in the production of epothilones and other therapeutically valuable compounds. The scheme above is provided for illustration and is not intended to limit the invention to particular compounds or synthetic methods. For example, compounds of formula (I) and (II) may be used for purposes other than synthesis of epothilones and/or may be made using synthetic methods other than those described herein. Similarly, epothilones and intermediates may be produced using processes in which additional synthetic steps are carried out biosynthetically rather than by chemical synthesis.

In one embodiment of the invention, the compound of formula (I) is 2-methyl-3-pentenoate N-acetylcysteamine thioester (also called (E)-S-2-acetomidoethyl 2-methyl-3-penenethioate) and the compound of formula (II) is (5R,6S)-3,3,5-trimethyl-6-((S,E)-pent-3-en-2-yl)-dihydro-3H-pyran-2,4-dione (Compound 1).

In related aspects the present invention provides novel compounds of formula (I) (structures are provided infra), novel compounds of formula (II), and host cells and methods for biotransformation of compounds of formula (I) to compounds of formula (II). These and many other aspects of the invention are described in detail below.

Compounds of Formula I

In one aspect, the present invention provides an isolated compound of formula (I).

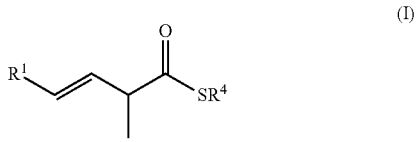

(I)

wherein $R^1$ is H, unsubstituted lower alkyl, or substituted lower alkyl; and $R^4$ is $C_1$-$C_{10}$ alkyl; or $R^4$ is $CH_2CO_2R^6$, wherein $R^6$ is lower alkyl; or $R^4$ is $CH_2CH_2NH(CO)R^5$, wherein $R^5$ is $C_1$-$C_{10}$ alkyl; with the proviso that the compound of formula (I) is not 3-pentenethioic acid, 2-methyl-, S-(1,1-dimethylethyl) ester (9CI) [CAS Reg. No. 103538-27-4]. In one embodiment, $R^4$ is not t-butyl. In one embodiment, $R^4$ is linear $C_1$-$C_{10}$ alkyl. With reference to formula (I) above $R^1$ and $R^6$ may also be $C_5$-$C_6$ alkyl as well as $C_3$-$C_6$ cycloalkyl. By "substituted" is meant that the group comprises one or more substituents, including but not limited to halogen, hydroxy, alkoxy, carboxy, carbalkoxy, carbonyl, amine, and alkylamine. In one embodiment $R^1$ is methyl. In one embodiment $R^4$ is $CH_2CH_2NHC(=O)CH_3$. In one embodiment the compound of formula (I) is 2-methyl-3-pentenoate N-acetylcysteamine thioester.

Compounds of formula (I) may be prepared using methods known in the chemical art, for example through alpha-methylation of 2-alkenoic or 3-alkenoic acids. For example, treatment of either $R^1$—CH=CH—$CH_2$—COOH or $R^1$—$CH_2$—CH=CH—COOH with two molar equivalents of a strong base, for example lithium diisopropylamide or lithium bis(trimethylsilylamide), at low temperature followed by treatment with a methylating reagent, for example iodomethane or dimethylsulfate, yields 2-methyl-3-pentenoic acid. One example is illustrated below in Example 1A. Alternatively, esters of the isomeric 2-methyl-2-pentenoate can be isomerized to the 2-methyl-3-pentenoates using strong base, followed by acid hydrolysis of the ester as illustrated in Example 2. Such acids are readily converted into their thioesters by reaction with a condensing agent, for example a carbodiimide such as dicyclohexyl-carbodiimide (DCC), and a thiol $R^4SH$, wherein $R^4$ is as described above. Alternately, the acids may be converted into their acid chlorides through the action of thionyl chloride, oxalyl chloride, or similar reagents. Alternately, a salt of the acid, for example the lithium or sodium salt, may be reacted with thionyl chloride or oxalyl chloride to produce the acid chloride, or may be reacted with a chloroformate to produce a mixed carboxylic-carbonic anhydride. The acid chlorides are then reacted with a thiol $R^4SH$, typically in the presence of a weak base such as pyridine, triethylamine, diisopropylethylamine, or the like. The mixed carboxylic-carbonic anhydrides are reacted with thiols in the presence of catalytic base. Examples are illustrated below in Example 1B and Example 2.

When used in the biosynthetic methods of the present invention, compounds of formula (I) may be either specific enantiomers, in particular for epothilones the (2S)-enantiomer, or they may be racemic. In the case of racemic compounds of formula (I), selection of the appropriate enantiomer during bioconversion yields the appropriate enantiomer of the compound of formula (II). It will be appreciated that uses of compounds formula (I) are not limited to the methods described herein, and that such compounds may be used in, for example, other biosynthetic and conventional syntheses.

Compounds of Formula II

In one embodiment of the invention, compounds are provided having the following formula (II):

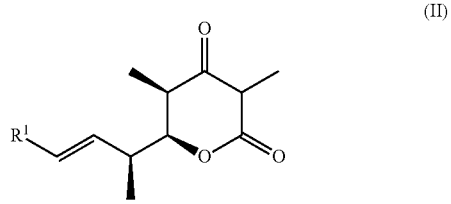

(II)

wherein $R^1$ is H, unsubstituted lower alkyl, or substituted lower alkyl. In one particular embodiment, compounds of formula (I) wherein $R^1$ is H or unsubstituted lower alkyl. In particular embodiments of the invention, compounds selected from the group consisting of Biosynthesis of Compounds of Formula (II)

In another aspect, the present invention provides methods for preparing compounds of formula (II) through the fermentation of host cells comprising polyketide synthases capable of converting compounds of the formula (I) to compounds of formula (II). As illustrated in FIG. 1, a compound of formula (I) must be extended by two 2-carbon polyketide units to produce a compound of formula (II).

In specific embodiments the method involves biotransformation of a compound of formula (I) in which $R^1$ is methyl and/or $R^4$ is $CH_2CH_2NHC(=O)CH_3$. In one embodiment the compound of formula (I) is 2-methyl-3-pentenoate N-acetylcysteamine thioester.

In related aspects, the invention provides recombinant polyketide synthase modules, nucleic acids encoding such modules, bimodular polyketide synthases, and host cells comprising these proteins and/or nucleic acids. As used herein, "recombinant" refers to proteins and nucleic acids having an amino acid or nucleotide sequence not found in nature. Without limitation, production of recombinant nucleic acids may include de novo synthesis (e.g., as described in US 20040166567) as well as conventional recombinant DNA technology.

A. Polyketide Synthases

Polyketide synthases (PKSs) are large multifunctional enzymes that catalyze the synthesis of the carbon backbones polyketides (for reviews see Hutchinson and McDaniel, 2001, "Combinatorial biosynthesis in microorganisms as a route to new antimicrobial, antitumor and neuroregenerative drugs," *Curr Opin Investig Drugs* 2:1681-90; Staunton et al., 2001, "Polyketide synthesis: a millennium review" *Nat. Prod. Rep.* 18:380-416; and Carreras et al., 1997, "The Chemistry and Biology of Fatty Acid, Polyketide, and Nonribosomal Peptide Biosynthesis" *Topics in Chemistry* 188:85-126, each of which is incorporated by reference). Two major types of PKS enzymes are modular PKS and iterative (or "aromatic") PKS. Modular PKS enzymes are typically multiprotein complexes in which each protein contains multiple active sites, each of which is used only once during carbon chain assembly and modification. Iterative PKS enzymes are typically multi-protein complexes in which each protein contains only one or at most two active sites, each of which is used multiple times during carbon chain assembly and modification.

Modular PKS enzymes are so termed because they are organized into distinct units (or modules) that ultimately control the structure of a discrete two-carbon portion of the polyketide the structure. PKS enzymes generally contain (i) a loading domain (LD), (ii) a number of extender modules, (iii) and a releasing domain (which is also called a thioesterase domain (TE)). The two-carbon units are of the general formula (R—C=O) from which polyketides are synthesized and are generally referred to as starter units or extender units depending on whether the two carbon unit initiates the synthesis of the polyketide or extends (adds to) the growing polyketide chain during synthesis. Starter units bind to the loading domain and initiate the polyketide synthesis and (ii) extenders bind to the extender modules and extend the polyketide chain. Starter units and extender units are typically acylthioesters, most commonly acetyl-CoA, propionyl-CoA, and the like for starter units and malonyl-CoA, methylmalonyl-CoA, methoxymalonyl-CoA, hydroxymalonyl-CoA, ethylmalonyl-CoA, and the like for extender units.

Each module of a modular PKS contains three core domains needed for polyketide synthesis: an acyltransferase (AT) responsible for selecting and binding the appropriate extender unit, an acyl-carrier protein (ACP) responsible for carrying the growing polyketide chain, and a beta-ketoacyl-synthase (KS) responsible for condensing the extender unit onto the growing polyketide chain. Together, these core domains add a 2-carbon beta-ketothioester onto the growing end of the polyketide chain.

In addition, a module may contain a set of reductive domains responsible for modifying the beta-ketone produced by the core domains. If present, a ketoreductase (KR) domain reduces the beta-ketone to an alcohol of defined stereochemistry (see Reid et al., 2003, "A model of structure and catalysis for ketoreductase domains in modular polyketide synthases" *Biochemistry* 42:72-9, incorporated herein by reference). If present with a KR, a dehydratase (DH) domain eliminates the alcohol produced by the KR to form an alkene. If present with a DH and a KR, an enoylreductase (ER) domain reduces the alkene produced by the DH to form a saturated alkane. Other types of modification domains, such as methyltransferase (MT) domains, can also be present in a module. Domain function, domain boundaries and module boundaries are identified by art known means, such as by detection of sequence homology. See, e.g., Yadav et al., 2003 "SEARCH-PKS: a program for detection and analysis of polyketide synthase domains," *Nucleic Acids Research* 31:3654-58, incorporated herein by reference.

By exploiting the modular nature of naturally occurring PKSs, investigators have developed an array of techniques for producing non-naturally occurring PKSs by modifying, rearranging, and recombining functional PKS modules and domains to produce non-naturally occurring products. For background see, for example, Menzella et al., 2007, "Rational design and assembly of synthetic trimodular polyketide synthases" *Chem Biol.* 14:143-51; Chandran et al., 2006, "Activating hybrid modular interfaces in synthetic polyketide synthases by cassette replacement of ketosynthase domains" *Chem Biol.* 13:469-74; Menzella et al., 2006, "Redesign, synthesis and functional expression of the 6-deoxyerythronolide B polyketide synthase gene cluster" *J Ind Microbiol Biotechnol.* 33:22-8; Menzella et al., 2005, "Combinatorial polyketide biosynthesis by de novo design and rearrangement of modular polyketide synthase genes" *Nat. Biotechnol.* 23:1171-6; Carreras and Santi, 1998, "Engineering of modular polyketide synthases to produce novel polyketides" *Curr Opin Biotechnol.* 9:403-411; and U.S. Pat. Nos. 7,101,684; 7,001,748; and 6,461,838. Each of the aforelisted references is incorporated herein by reference.

Nucleotide sequences for a multiplicity of PKSs are known and facilitate their use in recombinant procedures. For example, the nucleotide sequences for genes related to the production of erythromycin are disclosed in U.S. Pat. No. 6,004,787 and U.S. Pat. No. 5,998,194; for avermectin in U.S. Pat. No. 5,252,474; for FK506 in U.S. Pat. No. 5,622,866; for rifamycin in WO98/7868; for spiramycin in U.S. Pat. No. 5,098,837. These are merely examples. Additional examples are found in WO 01/27284, U.S. Pat. No. 6,524,841, and US Patent Publications US2004/0166567, and are readily available by reference to the patent and scientific literature (including GenBank and similar databases). In addition, each year many additional PKSs are characterized and reported in the scientific and patent literature.

As described below, in one aspect the invention provides a method for producing a compound of formula (II) by fermentation of cells that express a bimodular polyketide synthase in the presence of a compound of formula (I).

B. Bimodular Polyketide Synthases

As illustrated in FIG. 1, a compound of formula (II) can be produced by extending a compound of formula (I) by two polyketide units. This can be accomplished by fermenting a suitable host in the presence of a compound of formula (I) and propionate (or other source of acyl units). In one example, the host cell expresses a non-natural polyketide synthase comprising two recombinant PKS modules and a recombinant thioesterase (TE) domain, and fermenting the cells. A synthase with two PKS modules and a TE domain can be referred to as a bimodule.

Methods for construction, synthesis and evaluation of non-natural PKS modules, and bimodular combinations are described in Menzella, 2005, "Combinatorial polyketide biosynthesis by de novo design and rearrangement of modular polyketide synthase genes," *Nature Biotechnol.* 23, 1171-1176, and in U.S. Patent Publications US 20040166567 and US 20050227316, both incorporated by reference for all purposes. Nonnatural PKS modules and bimodular combinations are produced by expression of polynucleotides the modules. Polynucleotide encoding nonnatural PKS modules can be prepared by any desired methods, including conventional recombinant methods and the synthetic methods described in the Menzella et al. and US 20040166567, supra. In the case of a bimodule, the two modules may be coexpressed from separate vectors in the host cell and associate with each other through interaction of interpeptide linkers at the C-terminus of the upstream (or "first") module and N-terminus of the downstream (or "second") module, as described in Menzella et al. supra. Alternatively, the two modules can be expressed as a fusion protein in which the modules are separated by a natural or artificial PKS intrapeptide linker. The TE domain is most conveniently expressed as a fusion protein including and downstream from the second module.

For synthesis of compounds of formula (II) from compounds of formula (I), a first PKS extension module adds a propionyl unit (via methylmalonyl-CoA) and reduces the resulting β-carbonyl unit to an alcohol. The second extension adds a propionyl unit (via methylmalonyl-CoA) but leaves the β-carbonyl unit intact. Characteristics of bimodular polyketide synthases suitable for the production of compounds of formula (II) are described in more detail below.

First Extension Module

As noted above, for synthesis of compounds of formula (II) from compounds of formula (I) the first PKS extension module must add a propionyl unit (via methylmalonyl-CoA) and reduce the resulting β-carbonyl unit to an alcohol, while introducing the indicated stereochemistry.

There are several PKS extension modules with sequences known in the art that are suitable for use as the first extension module in the invention. For example, as described in Example 4 below, modules 2, 5, and 6 from the erythromycin PKS, module 3 from the geldanamycin PKS, and module 6 from the soraphen PKS were found to be active at extending 2-methyl-3-pentenoate N-acetylcysteamine thioester to produce the triketide (2R,3S,4S,E)-2,4-dimethyl-3-hydroxy-5-heptenoic acid. As described below, the triketide may be converted by a second extension module to product a tetraketide of formula (II). For illustration and not limitation, other modules predicted to be suitable in the methods of the invention are provided in Table 1. The nucleic acid and polypeptide sequences of these modules are generally available in the scientific and patent literature. For convenience GenBank™ accession numbers have been provided for selected polyketide synthase gene clusters.

In some embodiments the first extension module has the domain structure KS-AT-KR-ACP. In some embodiments the module produces a "D" type polypeptide scaffold as described in Menzella, 2005, supra. Examples of such modules include, in addition to modules 2, 5, and 6 from the erythromycin PKS, module 3 from the geldanamycin PKS, and module 6 from the soraphen PKS, other modules listed in TABLE 1. While not all modules of this type are expected to be active, all modules may be readily tested for their suitability as described below in Example 4. In one embodiment the first extension module has the structure: $LN^{eryM5}$-eryM2-$LC^{eryM2}$. (In this disclosure the PKS source of a component is indicated by the first three letters of the PKS name; modules are named by their PKS source followed by the number of the module of the source; LM or TE are superscripted with the PKS source; LC, LN and LI are superscripted with the PKS source and module number.)

TABLE 1

| PKS Cluster | Module | GenBank Accession No. | Source Organism |
|---|---|---|---|
| narbomycin | 5 | AF521878 | *Streptomyces narbonensis* |
| methy-/pikro-mycin | 5 | AF079138 | *Streptomyces venezuelae* |
| erythromycin | 2 | NC_009142 (genome); X60379 | *Saccharopolyspora erythraea* |
| erythromycin | 5 | NC_009142 (genome); X60379 | *Saccharopolyspora erythraea* |
| erythromycin | 6 | NC_009142 (genome); X60379 | *Saccharopolyspora erythraea* |
| megalomicin | 2 | AF263245 | *Micromonospora megalomicea* |
| megalomicin | 5 | AF263245 | *Micromonospora megalomicea* |
| megalomicin | 6 | AF263245 | *Micromonospora megalomicea* |
| oleandomycin | 2 | AF237895 | *Streptomyces antibioticus* |
| oleandomycin | 5 | AF237895 | *Streptomyces antibioticus* |
| oleandomycin | 6 | AF237895 | *Streptomyces antibioticus* |
| lankamycin | 2 | NC_004808 | *Streptomyces rochei* 7434AN4; *S. violaceoniger*; *S. spinichromogenes* |
| lankamycin | 5 | NC_004808 | *Streptomyces rochei* 7434AN4; *S. violaceoniger*; *S. spinichromogenes* |
| lankamycin | 6 | NC_004808 | *Streptomyces rochei* 7434AN4; *S. violaceoniger*; *S. spinichromogenes* |
| tylosin | 6 | AF147703 | *S. fradiae* |
| angolamycin | 6 | | *Micromonospora capillata* |
| angolamycin | 6 | EU232693 | *Streptomyces eurythermus* |
| repromicin | 6 | | *S. eurythermus*; *S. phaeochromogenes* |
| juvenimicin | 6 | | *Micromonospora chalcea*; *M. capillata* |
| rosamicin | 6 | | *Micromonospora rosaria*; *M. capillata*; *M. fastidiosus* |
| mycinamicin | 6 | AB089954 | *Micromonospora griseorubida* FERM BP-705 |
| chalcomycin | 6 | AY509120 | *Streptomyces bikiniensis* strain NRRL 2737 |
| dihydrochalcomyin | 6 | AY118081 | *Streptomyces* sp. KCTC 0041BP |
| aldgamycin | 6 | | *S. lavendulae* |
| oligomycin | 2 | NC_003155 (genome) | *S.* sp. str. A171 |
| oligomycin | 13 | NC_003155 (genome) | *S.* sp. str. A171 |
| oligomycin | 15 | NC_003155 (genome) | *S.* sp. str. A171 |
| rutamycin | 2 | | *S. griseus*; *S. aureofaciens*; *S. rutgersensis* |
| rutamycin | 13 | | *S. griseus*; *S. aureofaciens*; *S. rutgersensis* |
| rutamycin | 15 | | *S. griseus*; *S. aureofaciens*; *S. rutgersensis* |
| 44-homooligomycin | 2 | | *S. bottropensis* |
| 44-homooligomycin | 13 | | *S. bottropensis* |
| 44-homooligomycin | 15 | | *S. bottropensis* |
| cytovaricin | 2 | | *S. diastatochromogenes* |
| cytovaricin | 12 | | *S. diastatochromogenes* |
| cytovaricin | 13 | | *S. diastatochromogenes* |
| epothilone | 6 | AF217189; AF210843 | *Sorangium cellulosum* strain So ce90 |
| soraphen | 6 | U24241 | *Sorangium cellulosum* So ce26 (and over 20 other strains) |
| sorangicin | 12 | | *Sorangium cellulosum* So ce12 |
| stigmatellin | 4 | AJ421825 | *Stigmatella auriantica* DW4/3-1(Sg |

TABLE 1-continued

| PKS Cluster | Module | GenBank Accession No. | Source Organism |
|---|---|---|---|
| | | a15) | |
| tolypomycin | 5 | | S. tolypophorus |
| actamycin | 10 | | S. sp E/784 |
| diastovaricin | 10 | | S. diastatochromogenes |
| naphthoquinomycin | 10 | | S. sp. S-1998 |

It will be understood that suitable modules are not limited to those discussed above. For example, modules with other domain combinations that provide the same product can be used. For example, a module containing a catalytically inactive domain may produce the same product as a similar module wholly lacking the domain.

Although expression of a module having an amino acid sequence substantially similar to that of a naturally occurring PKS module has certain advantages, this is not required. For example, a chimeric or modified polyketide synthase module may be used. Exemplary chimeric and modified modules may be constructed by deletion of a domain present in a naturally occurring counterpart module, inactivation of a domain (e.g., by mutation), and/or substitution of a domain with a domain from another PKS module (with may be from the same or a different organism). Recombinant methods for manipulating modular PKS genes to make hybrid PKS enzymes are known in the art and are described in U.S. Pat. Nos. 5,672,491; 5,843,718; 5,830,750; 5,712,146, all incorporated by reference. In one embodiment the synthetic methods described in US 20040166567 are used to produce modified or chimeric modules.

Second Extension Module

As noted above, for synthesis of compounds of formula (II) from compounds of formula (I) the second PKS extension module must add a propionyl unit (via methylmalonyl-CoA) but leave the β-carbonyl unit intact. While there are two possible stereochemistries of the methyl group introduced during the second extension, in practice rapid equilibration of the final β-ketoester results in loss of any stereochemical information introduced by the second PKS extension module.

There are several PKS extension modules with sequences known in the art that are suitable for use as the second extension module in the invention, for example, as described in Example 5, below, module 3 of the erythromycin PKS may be used. In some embodiments the second extension module has the domain structure KS-AT-ACP. In some embodiments the module produces a "G" or an "H" type polypeptide scaffold as described in Menzella et al., 2005, supra. Examples of such modules include, in addition to those described in Example 4, module 3 of the rapamycin PKS, and module 6 of the pikromycin PKS. In one embodiment the second extension module has the structure: $LN^{eryM3}$-eryM3-TE. For illustration and not limitation, other modules predicted to be suitable in the methods of the invention are provided in Table 2. The nucleic acid and polypeptide sequences of these modules are generally available in the scientific and patent literature; For convenience, GenBank accession numbers have been provided for selected polyketide synthase gene clusters. While not all modules of this type are expected to be active, all modules may be readily tested for their suitability as described below in Example 5.

TABLE 2

| PKS Cluster | Module | GenBank Accession No. or Reference | Source Organism |
|---|---|---|---|
| narbomycin | 3 | AF521878 | Streptomyces narbonensis |
| meth-/pikro-mycin | 3 | AF079138 | Streptomyces venezuelae |
| erythromycin | 3 | NC_009142 (genome); X60379 | Saccharopolyspora erythraea |
| megalomicin | 3 | AF263245 | Micromonospora megalomicea |
| oleandomycin | 3 | AF237895 | Streptomyces antibioticus |
| lankamycin | 3 | NC_004808 | Streptomyces rochei 7434AN4; S. violaceoniger; S. spinichromogenes |
| niddamycin | 4 | AF016585 | Streptomyces caelestis |
| carbomycin | 4 | | S. halstedii |
| platenomycin | 4 | | S. platensis |
| leucomycin | 4 | | S. kitasatoensis; S. hygroscopicus; S. narbonensis; S. platensis |
| midecamycin | 4 | | S. mycarofaciens |
| spiramycin | 4 | Pat. No. 5,098,837 | S. ambofaciens |
| maridomycin | 4 | | S. hygroscopicus/platensis |
| tylosin | 4 | AF147703 | S. fradiae |
| angolamycin | 4 | | Micromonospora capillata |
| repromicin | 4 | | S. eurythermus; S. phaeochromogenes |
| juvenimicin | 4 | | Micromonospora chalcea; M. capillata |
| rosamicin | 4 | | Micromonospora rosaria; M. capillata; M. fastidiosus |
| mycinamicin | 4 | AB089954 | Micromonospora griseorubida FERM BP-705 |
| chalcomycin | 4 | AY509120 | Streptomyces bikiniensis strain NRRL 2737 |
| dihydrochalcomyin | 4 | AY118081 | Streptomyces sp. KCTC 0041BP |
| aldgamycin | 4 | | S. lavendulae |
| hygrolidin | 3 | | S. griseus, S. hygroscopicus |
| formamicin | 3 | | Saccharothrix sp. MK27-91F2 |
| leucanicidin | 3 | | S. halstedii; S. olivaceus |
| viranamycin | 3 | | S. sp. CH41 |
| concanamycin | 4 | DQ149987 | Streptomyces neyagawaensis; S. diastatochromogenes |
| virustomycin | 4 | | S. sp. |

TABLE 2-continued

| PKS Cluster | Module | GenBank Accession No. or Reference | Source Organism |
|---|---|---|---|
| rapamycin | 3 | X86780 | *Streptomyces hygroscopicus* |
| rapamycin | 6 | X86780 | *Streptomyces hygroscopicus* |
| oligomycin | 4 | NC_003155 (genome) | *S.* sp. str. A171 |
| oligomycin | 12 | NC_003155 (genome) | *S.* sp. str. A171 |
| oligomycin | 14 | NC_003155 (genome) | *S.* sp. str. A171 |
| rutamycin | 12 | | *S. griseus*; *S. aureofaciens*; *S. rutgersensis* |
| rutamycin | 14 | | *S. griseus*; *S. aureofaciens*; *S. rutgersensis* |
| 44-homooligomycin | 12 | | *S. bottropensis* |
| 44-homooligomycin | 14 | | *S. bottropensis* |
| avermectin | 11 | NC_003155 (genome) | *S. avermitilis* |
| milbemycin | 11 | | *S. hygroscopicus* ssp. *aureolacrimosus* |
| soraphen | 8 | U24241 | *Sorangium cellulosum* So ce26 (and over 20 other strains) |
| stigmatellin | 7 | AJ421825 | *Stigmatella auriantica* DW4/3-1(Sg a15) |
| rifamycin | 3 | AF040570 | *Amycolatopsis mediterranei* S699; ATCC13685 |
| halomicin | 3 | | *Micromonospora halophytica* |
| tolypomycin | 3 | | *S. tolypophorus* |
| actamycin | 3 | | *S.* sp E/784 |
| naphthoquinomycin | 3 | | *S.* sp. S-1998 |
| diastovaricin | 3 | | *S. diastatochromogenes* |

It will be understood that suitable modules are not limited to those discussed above. For example, modules with alternative domain structures that provide the same product can be used. For example, chimeric or modified polyketide synthase modules, or modules containing catalytically inactive domains, may be used as described above. As one example, a module with the structure KS-AT-KR*-ACP can be used, where KR* is catalytically inactive, may be used. As another example, a chimeric or modified polyketide synthase TE Domains Similarly, there are several thioesterase domains with sequences known in the art that may be suitable for termination of the polyketide chain, including for example the TE domains from the erythromycin, tylosin, epothilone, pikromycin, soraphen and pikromycin PKSs.

Linkers

Growth of the polyketide chain requires its transfer from the ACP of one module to the ketosynthase of the next. Both intra- and interpolypeptide acyl chain transfers occur, promoted by appropriate linkers to facilitate proximity. Intrapolypeptide linkers (LI) are spacers of ~20 amino acids separating the ACP of one module from the ketosynthase of the next. Interpolypeptide linkers (LN, LC) consist of an approximately 80-130 amino acid region at the C-terminal of one module that interacts with a cognate region of about 30-50 amino acids at the N-terminus of the downstream module. Importantly, linker sets cause productive module-module interactions between foreign module pairs. See, e.g., Broadhurst et al., 2003, "The structure of docking domains in modular polyketide synthases" *Chem. Biol.* 10:723-31; Wu et al., 2002, "Quantitative analysis of the relative contributions of donor acyl carrier proteins, acceptor ketosynthases, and linker regions to intermodular transfer of intermediates in hybrid polyketide synthases" *Biochemistry* 41:5056-66; Wu et al., 2001, "Assessing the balance between protein-protein interactions and enzyme-substrate interactions in the channeling of intermediates between polyketide synthase modules," *J Am Chem Soc.* 123:6465-74; and Gokhale et al., 1999, "Dissecting and exploiting intermodular communication in polyketide synthases" *Science* 284, 482-485; Gokhale et al., 2000, "Role of linkers in communication between protein modules" *Curr Opin Chem Biol.* 4:22-7; Tsuji et al., 2001, "Selective protein-protein interactions direct channeling of intermediates between polyketide synthase modules" *Biochemistry* 40:2326-31. Multiple modules may be expressed as a single fusion protein with modules separated by intrapeptide linker(s) or, more usually, as separate polypeptides that associate via interpeptide linkers. For construction of polyketide synthases which contain more than one polypeptide, the appropriate sequence of transfers can be accomplished by matching the appropriate C-terminal amino acid sequence of the donating module with the appropriate N-terminal amino acid sequence of the interpolypeptide linker of the accepting module. This can be done, for example, by selecting such pairs as they occur in native PKS. For example, two arbitrarily selected modules could be coupled using the C-terminal portion of module 4 of DEBS and the N-terminal of portion of the linking sequence for module 5 of DEBS. Alternatively, novel combinations of linkers or artificial linkers can be evaluated and used. Linkers may be tested for compatibility as described in the Examples below and in the scientific literature. It is usually convenient to use linker pairs known to be compatible in nature.

C. Host Cells and Expression Systems

Bimodular PKSs can be expressed in a variety of host cells. Generally, each module is encoded in a separate plasmid and two (or more) plasmids are introduced into a host cell. In order to obtain similar levels of expression for both genes, two plasmids with compatible origins of replications are preferred. For example, in the production of the tetraketide described in Example 6, plasmids maintained at about 20-30 copies per cell were used. The expression of both genes was under the control of the IPTG inducible T7 promoter. Alternatively two or more modules can be encoded on a single plasmid. In this case, the modules can be expressed as separate polypeptides or as a fusion protein as discussed above.

A variety of host cells may be used. Suitable host cells may express endogenous enzymes needed to support production of polyketides or such enzymes may be provided by expression of exogenous genes. Some host cells are natural polyketide producers including actinomycetes, such as members of the genus *Streptomyces*. Alternatively or additionally, host cells may be recombinantly engineered, for example, by the introduction of genes encoding appropriate holo-ACP synthases and enzymes required for the biosynthesis of polyketide building blocks such as methylmalonyl-CoA. Without intending to limit the invention suitable expression hosts include actinomycetes such as *Streptomyces* and *Saccharopolyspora*, strains of *Pseudomonas*, myxobacteria such as *Myxococcus xanthus* and *Sorangium cellulosum*, and yeasts such as *Saccharomyces*. Engineering of host cells to support polyketide production is known in the art, as described for example in U.S. Pat. Nos. 7,078,233 (Production of polyketides in bacteria and yeast); 6,838,265 (Overproduction hosts for biosynthesis of polyketides); 6,177,262 (Recombinant host cells for the production of polyketides); 5,672,491; 6,258,566; 6,838,265; and 7,011,959 (each of which is incorporated herein by reference). The working examples detailed below describe the expression of suitable PKS modules in *Escherichia coli* host cells that have been engineered to support the production of polyketides as described in Murli et al., 2003, "Metabolic engineering of *Escherichia coli* for improved 6-deoxy-erythronolide B production," *J. Ind. Microbiol. Biotechnol.* 30, 500-509 (incorporated herein by reference).

E. Fermentation Conditions

Methods for production of polyketides by fermentation of cells expressing PKSs are well known and described in the Examples below. Also see, for example, Pfeifer et al., 2002, Process and Metabolic Strategies for Improved Production of *Escherichia coli*-Derived 6-Deoxyerythronolide *Appl Environ Microbiol.* 68: 3287-92; U.S. Pat. Nos. 7,078,233; 6,838,265; 6,177,262; 5,672,491; 6,258,566; 6,838,265; and 7,011,959 (each of which is incorporated herein by reference).

F. Synthesis of Epothilone Analogs

Compound 1 is an intermediate in preparation of compounds that are intermediates in production of epothilones and other therapeutically valuable compounds. In one embodiment an epothilone precursor (Compound IX) is prepared according to the following synthetic scheme:

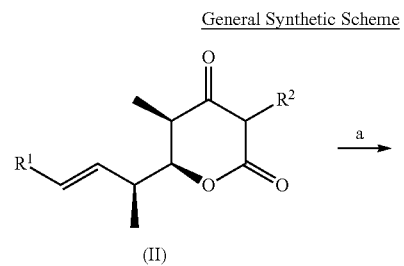

General Synthetic Scheme $R^1$ is H, unsubstituted lower alkyl, or substituted lower alkyl; $R^2$ and $R^3$ are each methyl; $R^4$ is $C_1$-$C_{10}$ alkyl; or $R^4$ is $CH_2CO_2R^6$, wherein $R^6$ is lower alkyl; or $R^1$ is $CH_2CH_2NH(CO)R^5$, wherein $R^5$ is $C_1$-$C_{10}$ alkyl; Pg is a hydroxy protecting group, and Aux is a chiral auxiliary which produces a diastereomeric ratio in favor of an S-configuration at the carbon bearing the hydroxy group. In preferred embodiments, $R^2$ is methyl. In other preferred embodiments, $R^1$ is selected from H and unsubstituted lower alkyl, more preferably selected from H, methyl and ethyl. In still other preferred embodiments, $R^3$ is methyl. Still further preferred are those embodiments in which $R^1$, $R^2$ and $R^3$ are each methyl. With reference to the Examples, below, and the synthetic scheme, above, a compound of Formula (II') [$R^1$=methyl, $R^2$=methyl; $R^3$=H] is produced biosynthetically (see Example 7). A compound of Formula (II) [$R^1$=methyl, $R^2$=methyl; $R^3$=methyl] is then synthesized as described in U.S. provisional application No. 60/917,572, and copending patent application Ser. No. 12/117,876 (filed 9 May 2008), the entire content of which is incorporated by reference herein.

Figure 3:
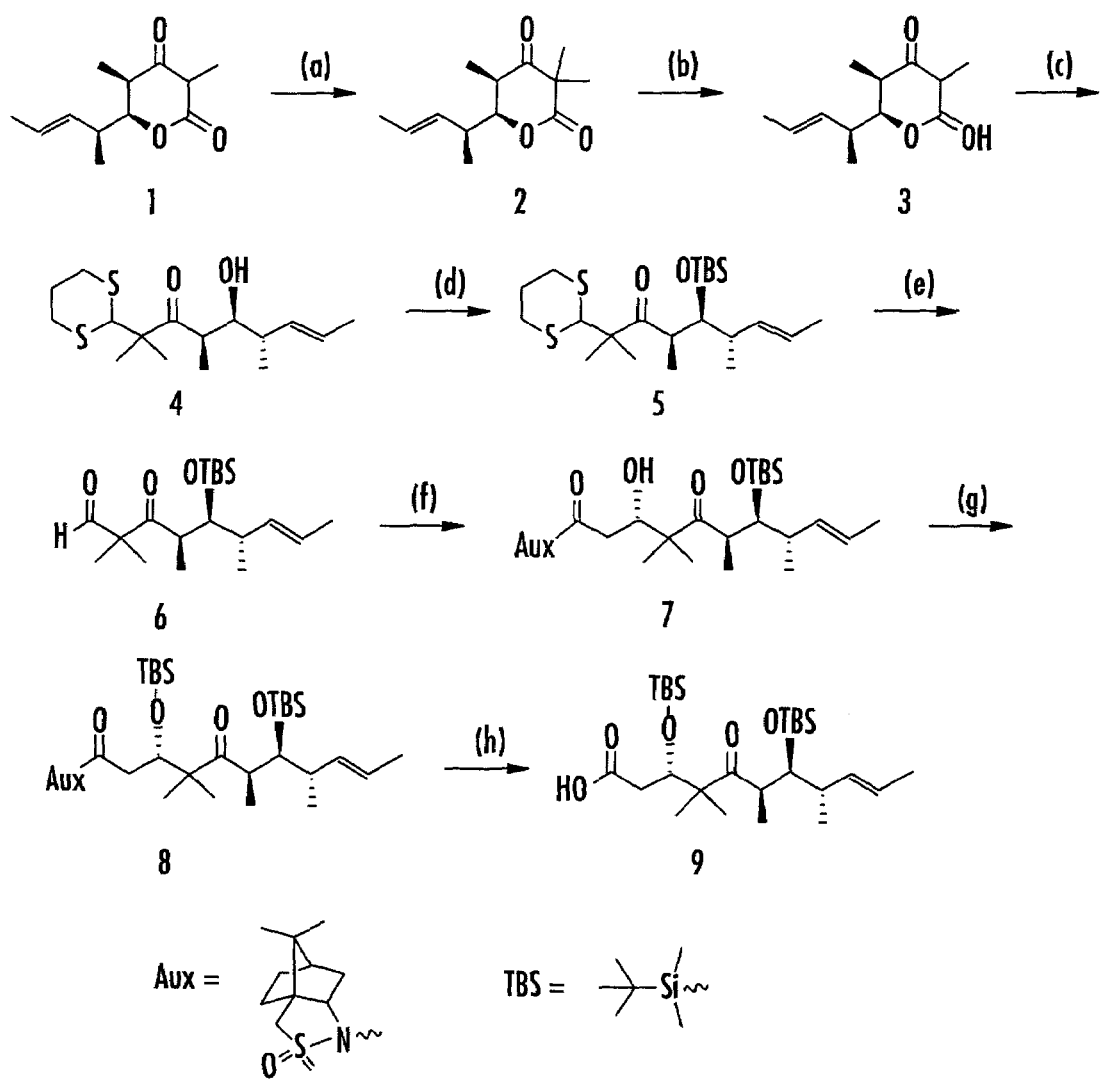
FIG. 3 illustrates a series of chemical transformations by which a compound of formula (II) is converted to a compound of formula (III). Specifically, the fermentation product (5R, 6S)-3,3,5-trimethyl-6-((S,E)-pent-3-en-2-yl)-dihydro-3H-pyran-2,4-dione (Compound 1) is chemically converted into (3S,6R,7S,8S,E)-3,7-bis(tert-butyldimethyl-silyloxy)-4,4,6,8-tetramethyl-5-oxoundec-9-enoic acid (Compound 9), an intermediate in the chemical synthesis of epothilones. Reagents and conditions employed in such transformations include: (a) $KO^tBu$, MeI, DMF, 60° C.; (b) diisobutylaluminum hydride, $CH_2Cl_2$, −78° C.; (c) 1,3-propanedithiol, $BF_3.OE^t{}_2$, $CH_3NO_2$, −20° C.; (d) $^t$butyldimethylsilyl triflate, 2.6-lutidine, $CH_2Cl_2$; (e) [bis(trifluoroacetoxy)] iodobenzene, $CH_3Cn, H_2O$; (f) (N-acetyl)-(2R)-bornane-10,2-sultam, dibutylboron triflate, diisopropylethylamine, $CH_2Cl_2$, −78° C.; (g) $^t$butyldimethylsilyl triflate, 2.6lutidine, $CH_2Cl_2$; (h) LiOH, $H_2O_2$, tetrahydrofuran.
Figure 4:
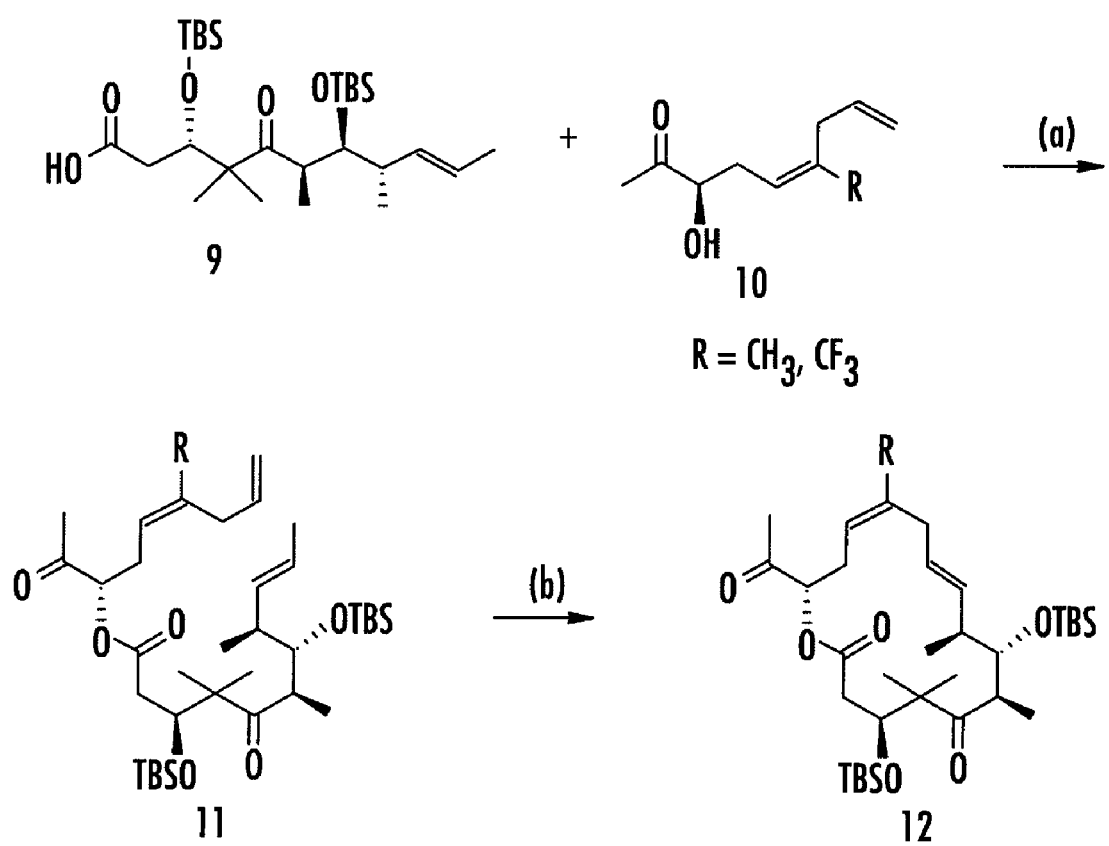
FIG. 4 illustrates one method for the conversion of (3S,6R, 7S,8S,E)-3,7-bis(tert -butyldimethylsilyloxy)-4,4,6,8-tetramethyl-5-oxoundec-9-enoic acid (Compound 9) into (4S, 7R, 8S, 9S, 10E, 13Z, 16S)-4,8-dihydroxy-5,5,7,9,13-pentamethyl-16-[1-oxoethyl]oxa-cyclohexadeca-10,13-diene-2, 6-dione (Compound 12), an intermediate in the chemical synthesis of epothilones. Reagents and conditions employed for such conversion include: (a) 1-(3-dimethylaminpropyl)-3-ethylcarbodiimide.HCl4-(dimethylamino)pyridine, $CH_2Cl_2$; (b) (1,3-Bis-(2,4,6-trimethylphenyl)2,3-dihydro-1H-imidazol-2-ylidene)dichloro(3-phenyl-1H-inden-1ylidene)-(tricyclohexylphosphine)-ruthenium, toluene, 115° C.
Figure 5:
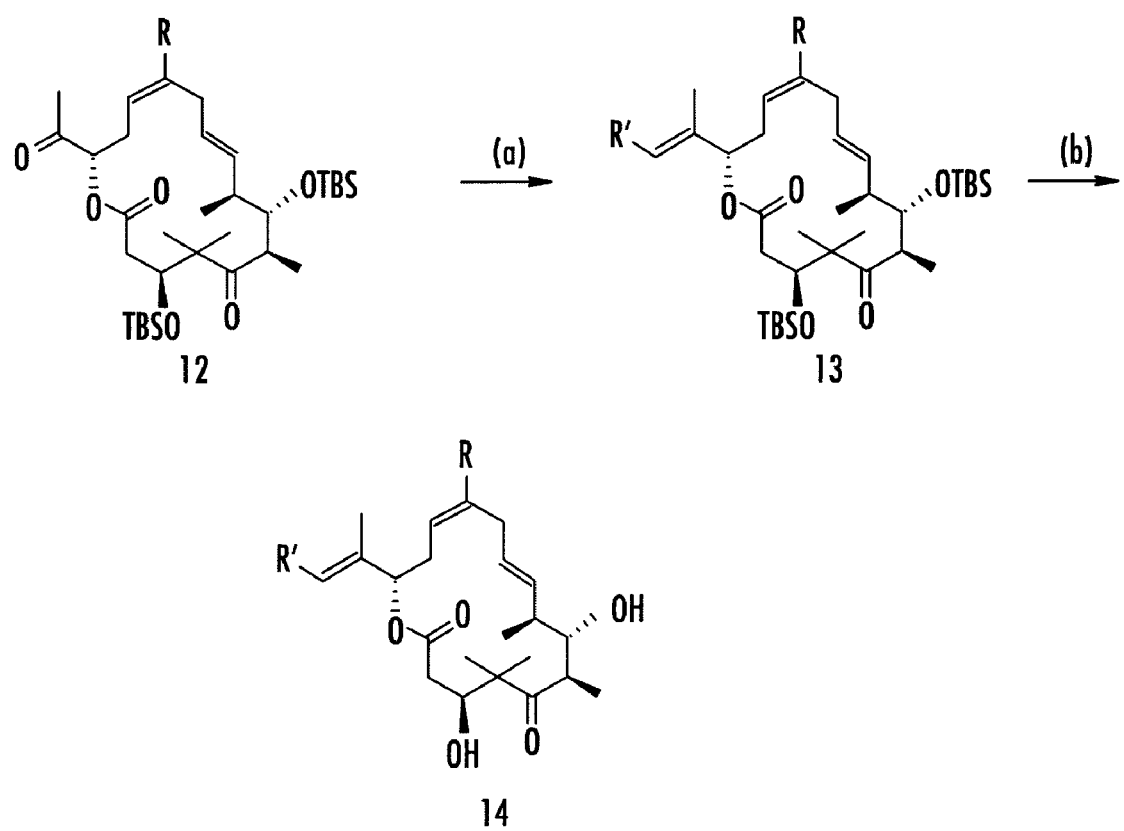
FIG. 5 illustrates one method for the conversion of (4S,7R,8S,9S,10E,13Z,16S)-4,8-dihydroxy-5,5,7,9,13-pentamethyl-16-[1-oxoethyl]-oxacyclohexadeca-10,13-diene-2,6-dione (Compound 12) into trans-9,10-dehydroepothilone D (Compound 14) and 26-trifluoro-trans -9,10-dehydroepothilone D. Reagents and conditions employed in such conversion include: (a) $Bu_3P=CHR'$; (b) HF.pyridine. R' is 2-methyl-4-thiazole.

In a particular embodiment an epothilone precursor is produced as shown in FIG. 3. FIGS. 4 and 5 illustrate additional synthetic steps by which the epothilone precursor produced in FIG. 3 (Compound 9) can be converted into 4S, 7R, 8S,9S, 10E, 13Z, 16S)-4,8-dihydroxy-5,5,7,9,13-pentamethyl-16-(1-oxoethyl) oxacyclohexadeca-10,13-diene-2,6-dione (Compound 14), an exemplary epothilione analog with therapeutic properties. Analogous methods for producing epothilione analogs using Compound (IX) (shown in the General Synthetic Scheme above) are described in detail in U.S. provisional application No. 60/917,572 and the above-referenced opending application.

G. EXAMPLES

Example 1

Synthesis of 2-methyl-3-pentenoate N-acetylcysteamine thioester ((E)-S-2-acetomidoethyl 2-methyl-3-penenethioate)

Examples 1A and 1B illustrate preparation of a compound of formula (I). In the example, 2-methyl-3-pentenoate N-acetylcysteamine thioester is prepared via a 2-methyl-3-pentenoic acid intermediate. As discussed herein, compounds of formula (I) are useful in biosynthesis of compounds of formula (II).

Example 1A

Synthesis of 2-methyl-3-pentenoic acid

A 1.0 M solution of lithium bis(trimethylsilyl)amide in tetrahydrofuran (THF, 24.5 mL) in 80 mL of freshly distilled THF was cooled to 0° C. and treated with a solution of 3-pentenoic acid (1.0 mL) in 5 mL of THF dropwise over a period of 10 minutes. After stirring for an additional 90 min at 0° C., methyl iodide (1.84 mL) was added and the mixture was allowed to warm to ambient temperature and kept for an additional 1 h. The reaction was quenched by addition of water/THF (1:1 v/v), acidified with 1 N HCl, and extracted with ether. The extract was washed sequentially with 1 N HCl, water, sat. aq. sodium thiosulfate, and brine, then dried over MgSO$_4$, filtered, and concentrated to provide 0.96 g of product. $^1$H-NMR (400 MHz, CDCl$_3$): δ 5.56 (2H, m), 3.10 (1H, dq), 1.69 (3H, dd), 1.26 (3H, d).

Example 1B

Synthesis of 2-methyl-3-pentenoate N-acetylcysteamine thioester 2-methyl-3-pentenoic acid (575 mg) was dried by concentration twice from benzene, then dissolved in 16 mL of dichloromethane. Thionyl chloride (1.1 mL) was added and the mixture was heated at 43° C. for 30 min. The mixture was evaporated to provide the crude acid chloride. The acid chloride was dissolved in 2.5 mL of benzene and cooled to 15-20° C., and a solution of N-acetylcysteamine (0.54 mL) and pyridine (0.52 mL) in dichloromethane (55 mL) was added dropwise. After 30 min, an additional portion of N-acetylcysteamine (0.54 mL) was added. After an additional 10 min, the mixture as diluted with dichloromethane and washed twice with 1 N HCl, water, and brine, then dried over MgSO$_4$, filtered, and evaporated. The crude product was chromatographed on silica gel (152 g) topped with CuSO$_4$-impregnated silica gel (27 g) using 60% ethyl acetate/hexanes to provide the purified thioester. $^{13}$C-NMR (100 MHz, CDCl$_3$): d 206, 170.2, 129.2, 128.8, 51.8, 39.6, 28.3, 23.1, 17.9, 17.5.

Example 2

Synthesis of 2-methyl-3-pentenoate N-acetylcysteamine thioester ((E)-S-2-acetamidoethyl 2-methyl-3-pentenethioate)

This example shows another method for synthesis of 2-methyl-3-pentenoate N-acetylcysteamine thioester.

Step 1. Ethyl 2-methyl-3-pentenoate

A dry, 12-L flask fitted with a mechanical stirrer, dropping funnel, and low temperature thermometer was charged with anhydrous THF (2800 mL) and diisopropylamine (438 mL), placed under N$_2$, and cooled on ice/methanol until the internal temperature was approximately 10° C. A solution of n-butyllithium (2.5 M/hexane, 1240 mL) was then added dropwise such that the temperature remained below 15° C. After addition was completed, the dropping funnel was rinsed with 20 mL of dry THF. The mixture was stirred for 15 minutes, then cooled on dry ice/acetone to −60° C. N,N'-dimethyl-propyleneurea (DMPU, 679 mL) was added dropwise such that the temperature remained at −60° C., and the resulting thick white slurry was stirred for an addition 1 h at −60° C. Ethyl 2-methyl-2-pentenoate (400 g) was added dropwise at −60° C., and the resulting solution was stirred for 30 minutes. Acetic acid (197 mL) was then added in a rapid stream, and the thick mixture was allowed to warm to ambient temperature. Water (~1000 mL) was added to dissolve the solids, and the phases were separated. The aqueous phase was extracted twice with ether (2000 mL each), and the combined organic phases were washed with sequentially with 1N HCl (3×1.5 L), water (3×2 L), and brine (1×2 L). The resulting solution was dried over MgSO$_4$, filtered, and concentrated at low temperature to provide the product (400 g, 100%) as a yellow oil.

Step 2. Sodium 2-methyl-3-pentenoate

Ethyl 2-methyl-3-pentenoate (400 g) was dissolved in methylsulfoxide (4000 mL) in a 12-L flask fitted with mechanical stirrer, heating mantle, internal thermocouple, and reflux condenser. A solution of H$_2$SO$_4$ (302 mL) in water (1990 mL) was added, and the mixture was heated at 100° C. for 2 hours. After cooling to ambient temperature, the mixture was extracted with 6-L of ether. The aqueous phase was back-extracted with ether (3×3 L). The organic extracts were combined, washed with water (3×3 L) and brine (1×3 L), then dried over MgSO$_4$, filtered and evaporated using a 20-L flask to provide the crude acid as a yellow oil (301.8 g, 94%). A small sample (~1 g) of the crude acid was set aside, and the remainder was stirred while a 25% solution of sodium methoxide in methanol (~572 mL) was added. A color change was noted upon complete neutralization of the acid, at which time the reserved acid was added back to the point where the dark color dissipated. The resulting solution was evaporated on the rotovap to remove most methanol, warming the rotovap bath to 50° C. Acetonitrile (2000 mL) was added rapidly to the warm flask while spinning, resulting in crystallization of the sodium salt. The mixture was allowed to spin for 30 minutes, then the flask was removed from the rotovap, flushed with dry nitrogen, closed, and allowed to cool to ambient temperature overnight. The solid material was scraped from the walls of the flask, mixed thoroughly in the liquid acetonitrile, then collected by vacuum filtration. During filtration, the funnel was blanketed with dry nitrogen. Due to the hygroscopic nature of the salt, exposure to sir should be minimized. The solid was rinsed quickly with cold acetonitrile, then dried under vacuum to give the sodium salt as a white hygroscopic solid (292 g, 81%).

Step 3. 2-methyl-3-pentenoate N-acetylcysteamine thioester

A 12-L flask fitted with mechanical stirrer, thermometer, and addition funnel was charged with N,S-diacetylcysteamine (322 g) and 2 N NaOH (2667 mL) and placed under $N_2$ atmosphere. The mixture was stirred for 30 min at ambient temperature, then placed in a water bath and 6 N HCl (271 mL) was added to provide a solution of thiolate.

Simultaneously, a 12-L 3NRB flask fitted with mechanical stirrer, addition funnel, and thermometer, was charged with dichloromethane (7000 mL) and methyl chloroformate (526 mL), and cooled using an ice bath. A solution of sodium 2-methyl-3-pentenoate (310 g) and tetrabutylammonium bromide (14.6 g) in water (2500 mL) was added over a period of 1 hour with vigorous stirring. After an additional hour, the organic phase was separated. The aqueous phase was extracted with $CH_2Cl_2$ (1×1 L). The combined organic solutions were washed with water (1×4 L) and brine (1×4 L), then dried over $MgSO_4$, filtered, and evaporated using the rotovap while keeping the bath temperature below 25° C. This yielded methyl 2-methyl-3-pentenoyl carbonate as an unstable colorless oil (346 g), which was used immediately.

The yielded methyl 2-methyl-3-pentenoyl carbonate was added in a slow stream to the thiolate solution from above. Gas evolution was noted, and the mixture was vigorously stirred for an additional 1 hour after addition was complete. The mixture was diluted with ethyl acetate (4000 mL), and the phases were separated. The aqueous phase was extracted with ethyl acetate (2×4 L), and the organic phases were combined and washed sequentially with water and brine. After drying over $MgSO_4$, the solution was filtered and evaporated on the rotovap to provide the crude thioester (376 g).

The crude product was dissolved in a minimal amount of $CH_2Cl_2$, then loaded onto silica gel (1500 g) equilibrated with 25% ethyl acetate/hexanes. The silica was washed with 25% ethyl acetate/hexanes (1 L), 50% ethyl acetate/hexanes (4 L), 90% ethyl acetate/hexanes (4 L), and ethyl acetate (1 L). The product-containing fractions were pooled and concentrated. Partially-purified side fractions were combined, concentrated, and resubmitted to silica purification. The pure fractions were combined to provide the product, 315 g (73%).

Example 3

Construction of strains producing (5R,6S)-3,5-dimethyl-6-((S,E)-pent-3-en-2-yl)-dihydro-3H-pyran-2,4-dione This example shows describes production of recombinanat *E. coli* cells expressing a bimodular PKS having the structure $LN^{eryM5}$-eryM2-$LC^{eryM2}$-$LN^{eryM3}$-eryM3-TE These cells are able to effect the biosynthesis of Compound 1 from a 2-methyl-3-pentenoate N-acetylcysteamine thioester precursor. The cells were prepared by cotransfection with two plasmids, pKOS501-174-1 and pKOS422-175-1. The construction of these plasmids is described, as are the transformation and fermentation of the resultant cells.

*Escherichia coli* DH5α was used for routine plasmid DNA preparation. DNA manipulations were performed using standard methods. The plasmids used are listed in TABLE 3. The inserts for the synthetic plasmids MGP001, MGP003, MGP007, MGP009, MGP010, MGP011, MGP023, MGP038, MGP059, MGP063 and MGP066 were made following the procedure described in US published patent application US 20040166567, and Menzella et al., 2007, "Rational design and assembly of synthetic trimodular polyketide synthases" *Chem. Biol.* 14:143-51 (including Supplementary Tables) which is incorporated herein in its entirety by reference. Restriction sites were included in the synthetic sequence to facilitate cloning.

TABLE 3

| Plasmid | Replicon/Resistance | Insert |
| --- | --- | --- |
| MGP001 | ColE1/Carb | eryM2 |
| MGP009 | ColE1/Carb | $LN^{eryM5}$ |
| pKOS422-167-1 | ColE1/Carb | $LN^{eryM5}$-eryM2 |
| MGP011 | ColE1/Carb | $LC^{eryM2}$ |
| pKOS422-167-5 | ColE1/Carb | $LN^{eryM5}$-eryM2-$LC^{eryM2}$ |
| pCDF-1b | CloDF13/Str | Empty expression vector (Novagen) |
| pKOS501-174-1 | CloDF13/Str | $LN^{eryM5}$-eryM2-$LC^{eryM2}$ |
| MGP003 | ColE1/Carb | TE |
| MGP007 | ColE1/Carb | $LN^{eryM3}$-eryM3 |
| pKOS422-167-6 | ColE1/Carb | $LN^{eryM3}$-eryM3-TE |
| pET28a | ColE1/Km | Empty expression vector (Novagen) |
| pKOS422-175-1 | ColE1/Km | $LN^{eryM3}$-eryM3-TE |
| MGP009 | ColE1/Carb | $LN^{eryM5}$ |
| MGP010 | ColE1/Carb | eryM6 |
| MGP038 | ColE1/Carb | sorM6 |
| MGP023 | ColE1/Carb | epoM7 |
| MGP059 | ColE1/Carb | gdmM3 |
| MGP063 | ColE1/Carb | lepM10 |
| MGP066 | ColE1/Carb | rifM5 |
| pKOS422-4 | ColE1/Km | $LN^{eryM3}$-MfeI-SpeI-TE |
| pKOS422-30-6 | ColE1/Km | $LN^{eryM3}$-eryM6-TE |
| pKOS422-30-2 | ColE1/Km | $LN^{eryM3}$-eryM2-TE |
| pKOS422-30-5 | ColE1/Km | $LN^{eryM3}$-eryM5-TE |
| pKOS422-107-1 | ColE1/Km | $LN^{eryM3}$-gdmM3-TE |
| pKOS422-99-4 | ColE1/Km | $LN^{eryM3}$-sorM6-TE |
| pKOS422-107-2 | ColE1/Km | $LN^{eryM3}$-lepM10-TE |
| pKOS422-107-3 | ColE1/Km | $LN^{eryM3}$-rifM5-TE |
| pKOS426-122-7 | ColE1/Km | $LN^{eryM3}$-epoM7-TE |

The plasmid pKOS501-174-1 was created as follows: (i) The MfeI-EcoRI fragment of MGP001 was cloned into the same sites of MGP009 to obtain the pKOS422-167-1, (ii) The NdeI-XbaI fragment of this plasmid was cloned into the NdeI-SpeI sites of the MGP011 to create the pKOS422-167-5, (iii) The resulting ORF was then mobilized as NdeI-EcoRI fragment to the same sites of the expression vector pCDF-1*b* (Novagen) to give the final plasmid. See FIG. 2.

The plasmid pKOS422-175-1 was created as follows: (i) The XbaI-EcoRI fragment of MGP003 was inserted into the SpeI-EcoRI of MGP007 to create the pKOS422-167-6, (ii) The resulting ORF was then mobilized as NdeI-EcoRI fragment to identical sites of the expression vector pET28a (Novagen). See FIG. 2.

The plasmids pKOS501-174-1 and pKOS422-175-1 were co-transformed into the *E. coli* polyketide production strain K207-3 strain [BL21ΔprpBCD::T7prom prpE, T7prom accA1-pccB, T7prom sfp] has been described; see Murli, S., Kennedy, J., Dayem, L. C., Carney, J. R., and Kealey, J. T. (2003), "Metabolic engineering of *Escherichia coli* for improved 6-deoxy-erythronolide B production," *J. Ind. Microbiol. Biotechnol.* 30, 500-509 (incorporated herein by reference) and selected on LB plates supplemented with antibiotics. The resulting colonies were grown in 5 ml of LB medium to an $OD_{600}$=0.5 and then induced by the addition of IPTG (0.5 mM final concentration) and supplemented with 2-methyl-3-pentenoate N-acetylcysteamine thioester (1 mM) (pre-dissolved in DMSO), sodium propionate pH 7 (5 mM), sodium glutamate pH 7 (50 mM), and sodium succinate pH 7 (50 mM). Cultures were further incubated for 72 h at 22° C. with agitation. Finally, 300 µl of the supernatants, acidified to pH 2.5 with 2 M sodium phosphate pH 1.5, were analyzed by LC/MS/MS as described in Menzella et al., 2005, *Nature Biotechnol.* 23, 1171-1176, which is incorporated herein by reference. LC/MS/MS analysis of the cultures after 72 h revealed the production of the tetraketide product. Titers of the product were estimated to be 12±2 mg/L using a synthetic standard. Aliquots were removed every 24 h and the expression of the recombinant proteins analyzed by PAGE.

Example 4

Selection of Module 1 of the Bimodular PKS

To detect modules with the ability to catalyze the first step of the reaction to produce the desired target, several open reading frames of the class $LN^{eryM3}$-ModX-TE where $LN^{eryM3}$ was the N-terminal peptide linker from module 3 of the erythromycin PKS, ModX was the PKS module to be tested, and TE was the thioesterase from the erythromycin PKS, were assembled in expression vectors. The plasmids used are listed in TABLE 3. A generic expression vector containing $LN^{eryM3}$ and TE separated by MfeI and SpeI sites was created as follows: (i) The NdeI-EcoRI fragment of the MGP009 was cloned into identical sites of the pET28a to obtain the pKOS422-4 plasmid, (ii) The SpeI-EcoRI fragment of MGP003 was cloned into the same sites of pKOS422-4 to obtain the pKOS422-28-2. Finally the MfeI-XbaI fragments of the plasmids MGP010, MGP001, MGP009, MGP059, MGP039, MGP063, MGP066 and MGP023 were cloned into the MfeI-SpeI sites of the pKOS422-28-2 to obtain the expression vectors pKOS422-30-6, pKOS422-30-2, pKOS422-30-5, pKOS422-107-1, pKOS422-99-4, pKOS422-107-2, pKOS422-107-3 and pKOS426-122-7 respectively.

The resulting plasmids were transformed into the *E. coli* strain K207-3 and the obtained transformants were grown and induced in the presence of 2-methyl-3-pentenoate N-acetylcysteamine thioester. Culture supernatants were analyzed by LC/MS/MS for the triketide product of the successful extension of the thioester, (2R,3S,4S,E)-2,4-dimethyl-3-hydroxy-5-heptenoic acid. The obtained results are shown in TABLE 4. The triketide was detected in the supernatants of six different cultures indicating the ability of the corresponding modules to successfully extend the thioester.

TABLE 4

Extension of thioester to produce triketide by modules expressed as $LN^{eryM3}$ModX-TE in *E. coli* strain K207-3.

| PKS | triketide production (mg/L) |
|---|---|
| $LN^{eryM3}$eryM6-TE | 20 |
| $LN^{eryM3}$eryM2-TE | 12 |
| $LN^{eryM3}$eryM5-TE | 2 |
| $LN^{eryM3}$gdmM3-TE | 1 |
| $LN^{eryM3}$sorM6-TE | 0.1 |
| $LN^{eryM3}$lepM10-TE | Trace |
| $LN^{eryM3}$rifM5-TE | Not detected |
| $LN^{eryM3}$epoM7-TE | Not detected |

Erythromycin modules 6 and 2 were the most efficient catalysts to extend the 2-methyl-3-pentenoate N-acetylcysteamine thioester.

eryM2 is naturally connected to a module capable of adding the G extension (eryM3), which was previously shown to be functional when connected to the erythromycin thioesterase (TE). Thus, we rationalized that a bimodular PKS comprising eryM2-eryM3-TE would be a good candidate to extend the Msh-SNAC to produce Compound 1 because the two extender modules are contiguous in the native PKS, avoiding the introduction of hybrid module-module interfaces that may result in lower product yields. Consequently, a system to express the latter bimodular PKS was created where the assembly line was housed in two proteins: the first one includes eryM2 flanked by the N terminal docking domain of eryM5 and its natural C terminal docking domain ($NL^{eryM5}$-eryM2-$CL^{eryM2}$) and the second one eryM3, with its natural N terminal docking domain and the DEBS TE at the C-term ($NL^{eryM3}$-eryM3-TE) (FIG. 1B).

It is thus possible to test candidate modules for suitability as module 1 in the bimodular PKS using the above-described assay.

Example 5

Selection of Module 2 of the Bimodular PKS

To detect modules with the ability to catalyze the second step of the reaction to produce the desired target, open reading frames of the class $LN^{eryM3}$-ModX-TE (where ModX is the extension module to be tested) can be assembled in expression vectors, described in Example 3 above, and co-transformed with a vector expressing the first extension module. For example, a vector encoding eryM2 flanked by the N terminal docking domain of eryM5 and its natural C terminal docking domain ($NL^{eryM5}$-eryM2-$CL^{eryM2}$) can be co-transfected with the vector encoding $LN^{eryM3}$-ModX-TE. Assays for production of the desired tetraketide (e.g., (5R,6S)-3,5-dimethyl-6-((S,E)-pent-3-en-2-yl)-dihydro-3H-pyran-2,4-dione) are used to determine whether the bimodule is productive.

Example 6

Figure 2:
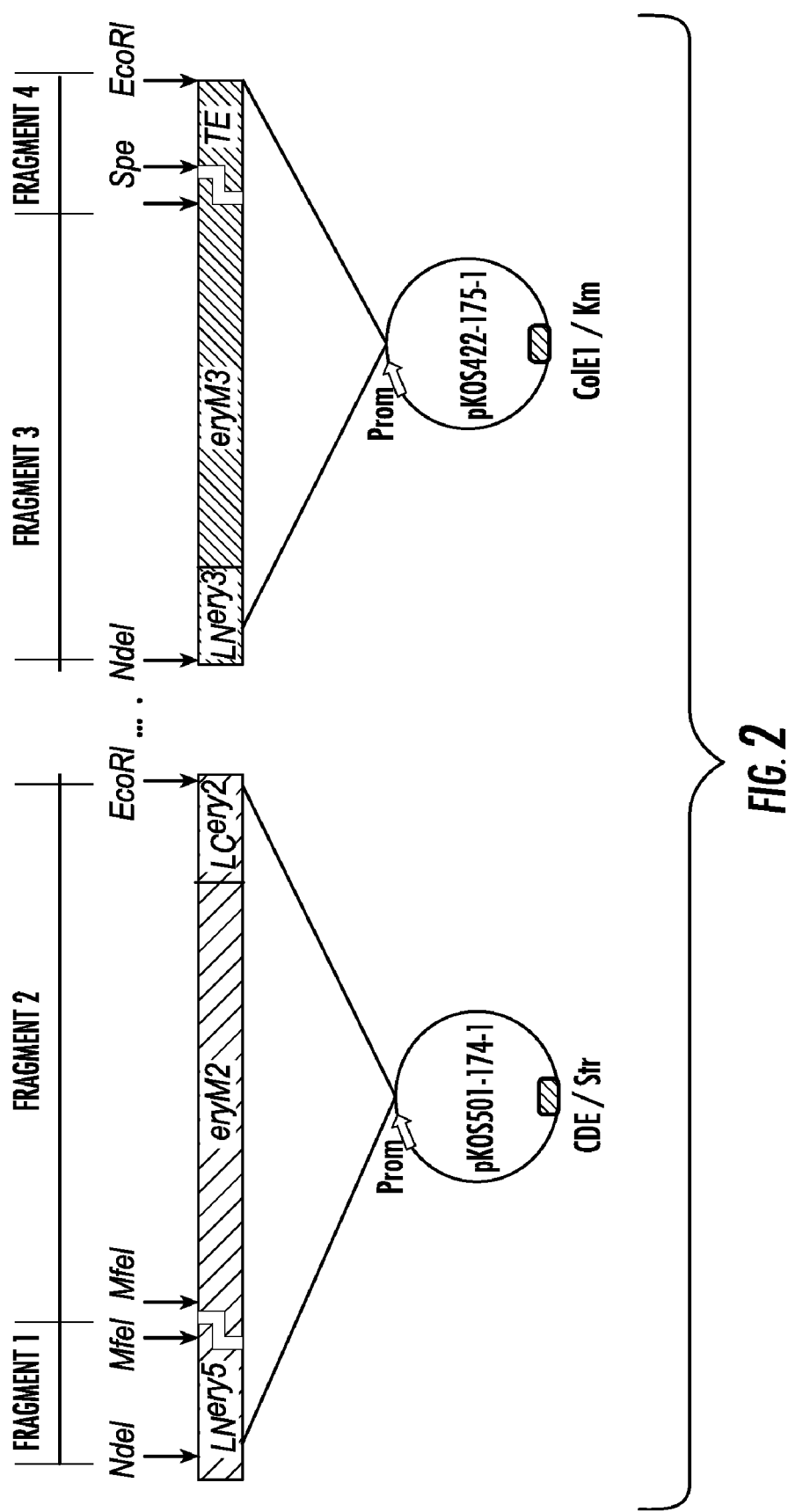
FIG. 2 illustrates one embodiment of the invention, showing two expression plasmids used to express a bimodular polyketide synthase for the production of (5R,6S)-3,3,5-trimethyl-6-((S,E)-pent-3-en-2-yl)-dihydro-3H-pyran-2,4-dione (Compound 1). Plasmid pKOS501-174-1 contains the open reading frame (ORF) for the expression of $NL^{eryM5}$-eryM2-$CL^{eryM2}$ protein inserted between the NdeI and EcoRI site of pCDF-1b (Novagen). Fragment1 comprises the bases 1 to 120 of the DEBS 3 synthetic gene (Genbank accession number AY771999). Fragment2 comprises the bases 6046 to 10636 of the DEBS 1 synthetic gene (Genbank accession number AY771999). Plasmid pKOS422-175-1 contains the ORF for the expression of $LN^{eryM3}$-eryM3-TE protein inserted between the NdeI and EcoRI site of pET28a (Novagen). Fragment3 comprises the bases 1 to 4412 of the DEBS 2 synthetic gene (GenBank Accession Number AY771999). Fragment4 comprises the bases 8680 to 9504 of the DEBS 3 synthetic gene (Genbank accession number AY771999).

Production of (5R,6S)-3,5-dimethyl-6-((S,E)-pent-3-en-2-yl)-dihydro-3H-pyran-2,4-dione Various strains as described in Example 3 may be used to produce (5R,6S)-3,5-dimethyl-6-((S,E)-pent-3-en-2-yl)-dihydro-3H-pyran-2,4-dione according to the methods of the invention. This Example illustrates the method using *Escherichia coli* K207-3 harboring the plasmids pKOS501-174-1 and pKOS422-175-1 (FIG. 2).

A 1-mL aliquot of frozen cells of *Escherichia coli* K207-3/pKOS501-174-1/pKOS422-175-1 maintained in 20% (v/v)

glycerol was used to inoculate a 250-mL baffled Erlenmeyer flask containing 50 mL of LB medium (tryptone, 10 g/L; yeast extract 10 g/L; NaCl 5 g/L), 50 μL of 50% (v/v) Antifoam B, 50 mg/L kanamycin, and 50 mg/L streptomycin. The culture was incubated at 37° C. with rotary shaking at 275 rpm for approximately 3 h until an $OD_{600}$ of 1.0-1.2 was reached, which provided the primary seed culture. Secondary seed cultures were generated by transferring 2.5 mL of the primary seed culture into 250-mL baffled Erlenmeyer flasks containing the same medium, then growing under the same conditions.

A 5-L bioreactor (B. Braun) containing 3 L of production medium, consisting of 5 g/L Bacto yeast extract (BD), 10 g/L casein digest type M (Marcor), 15 g/L glycerol, 10 g/L NaCl, 3 mL/L 50% (v/v) Antifoam B, and 100 mM HEPES, pH 7.0, was autoclaved at 121° C. for 60 min. After sterilization, 50 mg/L kanamycin, 50 mg/L streptomycin, 2 g/L sodium propionate, 0.5 g/L 2-methyl-3-pentenoate N-acetylcysteamine thioester, 10 μM β-alanine, and 100 μM isopropyl β-D-1-thiogalactopyranoside (IPTG). The kanamycin, streptomycin, sodium propionate, β-alanine, and IPTG were prepared in deionized water and filter-sterilized to provide stock solutions of 50 g/L, 100 g/L, 150 g/L, 100 mM, and 1 M, respectively. The thioester was prepared as a 400 g/L filter-sterilized stock solution in methyl sulfoxide (DMSO). The medium was then inoculated with 150 mL of secondary seed culture. The fermentation was maintained at 22° C. with an aeration rate of 0.3 v/v/m and an initial agitation rate of 400 rpm. The dissolved oxygen was controlled at 50% of air saturation by an agitation cascade between 400-1100 rpm. The culture pH was monitored but not controlled. Foaming was controlled by automated addition of 50% (v/v) Antifoam B. Production of product was monitored by removing aliquots of the culture and pelleting the cells by centrifugation. The supernatant (40 μL) was diluted with water (160 μL), and 80 μL of 2M phosphoric acid was added. The samples were then analyzed by LC/MS as described in Example 1. Production of the tetraketide product began on day 1, and the fermentation was continued until maximal product was observed on day 4.

Example 7

Purification of Tetraketide (5R,6S)-3,5-dimethyl-6-((S,E)-pent-3-en-2-yl)-dihydro-3H-pyran-2,4-dione The tetraketide (5R,6S)-3,5-dimethyl-6-((S,E)-pent-3-en-2-yl)-dihydro-3H-pyran-2,4-dione was isolated from fermentation broths of *E. coli* K207-3/pKOS501-174-1/pKOS422-175-1 grown as described in Example 6 using the following procedure.
The fermentation broth was adjusted to pH 2.5 with concentrated phosphoric acid and then was clarified by centrifugation. The undiluted supernatant was loaded at 1.6 L/min onto a pre-equilibrated (water+0.05% $H_3PO_4$) BPG300 column (14.8 cm×11 cm; 7.5 L of resin) packed with HP20SS and equipped with a 0.40 μm prefilter. The column was eluted at 1.6 L/min with 58:42 (v/v) methanol:water containing 0.1% acetic acid, followed by 63:37 (v/v) methanol:water containing 0.1% HOAc and fractions of column volumes (CV) were collected. The fractions were combined to generate two pools, one containing only unconverted thioester, and a second pool containing a mixture of unconverted thioester and tetraketide product.
The pool enriched in thioester was set aside and the pool containing the mixture of thioester and tetraketide product was diluted to 20% (v/v) methanol with water containing 0.1% HOAc. This was then loaded at 0.8 L/min onto a pre-equilibrated BPG200 column (10 cm×36.5 cm; 11.5 L resin; <1 g/L product loading) packed with BakerBond C18 resin. The column was eluted with 50:50 (v/v) methanol:water containing 0.1% acetic acid at 0.8 L/min and ¼ CV fractions were collected. Selected fractions from the C18 chromatography were combined in two pools. Pool 1 contained almost exclusively unconverted thioester along with a small amount of tetraketide product. Pool 2 contained thioester and tetraketide at a ratio of approximately 2:1.

Pool 2 from the C18 chromatography step was diluted to 30% (v/v) methanol with water containing 0.1% acetic acid. A pre-equilibrated solvent exchange column (10 cm×12 cm; 940 mL resin) packed with Bakerbond C18 was loaded at 0.8 L/min. The column was washed with 3 CV of water then with 2 CV of 30:70 (v/v) methanol:water. The product was eluted using 100% methanol at a flow rate of 0.8 L/min. The eluent was dried to solids then resuspended in 50 mL of methanol and filtered through a 0.22 μm membrane filter. The filtrate was dried (approximate solids purity of 60% in respect to unconverted thioester and tetraketide product) then resuspended in 7 mL of methanol for injection onto a preparative HPLC.

Samples were injected across a Varian Inertsil preparative HPLC column (300 mm×250 mm; 120 mg total tetraketide+thioester loading) equipped with an Inertsil guard column (20 mm×50 mm). The product was eluted with 45:55 (v/v) acetonitrile:water, 0.1% acetic acid, at a flow rate of 20 mL/min. The eluent was monitored at 248 nm and ½ CV fractions were taken. Fractions enriched in tetraketide product were combined and diluted to 20% (v/v) acetonitrile using water containing 0.1% acetic acid. This was then loaded at 40 L/min onto a pre-equilibrated C18 solvent exchange column (4.8 cm×11 cm; 200 mL resin) and washed with 3 CV of water followed by 2 CV of 30:70 (v/v) methanol:water. The column was eluted with 100% methanol and the material was dried affording a tan solid with purity >85%.

For analysis, samples containing unconverted thioester and tetraketide product were analyzed by HPLC on a Varian Inertsil C18 column (150×4.6 mm) equipped with a MetaGuard precolumn. The solvent system was 45:55 (v/v) acetonitrile:water, 0.1% acetic acid at a flow rate of 1.0 mL/min. The products were monitored by UV absorbance at 248 nm.

Using this procedure, the tetraketide (5R,6S)-3,5-dimethyl-6-((S,E)-pent-3-en-2-yl)-dihydro-3H-pyran-2,4-dione was isolated from two *E. coli* K207-3/pKOS501-174-1/pKOS422-175-1 fermentations: one 80-L culture containing 4.2 mg/L of product, and one 53-L culture containing 5.5 mg/L. Purification from the two fermentations resulted in 448 mg of TKL with purity >85%. The $^1$H-NMR and $^{13}$C-NMR spectra indicated that the product exists primarily as the ketoester in $CDCl_3$, but with observable signals from the enolester tautomer. Ketoester tautomer: $^1$H-NMR ($CDCl_3$): δ 5.3-5.7 (2H, m), 4.39 (1H, dd, J=3.2, 9.2 Hz), 3.58 (1H, q, J=6.4 Hz), 2.70 (1H, dq, J=2.8, 7.6 Hz), 2.50 (1H, m), 1.68 (3H, d, J=6.5 Hz), 1.32 (3H, d, J=6.8 Hz), 1.15, (3H, d, J=7.6 Hz), 1.01 (3H, d, J=7.2 Hz). $^{13}$C-NMR ($CDCl_3$): δ 205.4, 170.2, 131.2, 127.4, 81.3, 50.3, 43.2, 36.7, 18.0, 15.9, 9.8, 8.2.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for the preparation of a compound of formula (II):

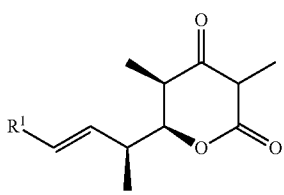

wherein $R^1$ is H, unsubstituted lower alkyl, or substituted lower alkyl;
the method comprising the steps of growing a host cell comprising a polyketide synthase in a medium comprising a thioester of formula (I)

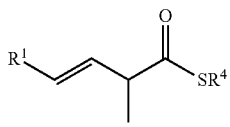

wherein $R^4$ is $C_1$-$C_{10}$ alkyl; or $R^4$ is $CH_2CO_2R^6$, wherein $R^6$ is lower alkyl; or $R^4$ is $CH_2CH_2NH(CO)R^5$, wherein $R^5$ is $C_1$-$C_{10}$ alkyl, under conditions wherein the polyketide synthase converts the thioester of formula (I) into the compound of formula (II).

2. The method of claim 1 further comprising isolating the compound of formula II.

3. The method of claim 1, wherein the thioester of formula (I) is a 2-methyl-3-pentenoate thioester.

4. The method of claim 3, wherein the thioester of formula (I) is 2-methyl-3-pentenoate N-acetylcysteamine thioester.

5. The method of claim 1, wherein said the polyketide synthase comprises a first extender module, a second extender module, and a thioesterase domain.

6. The method of claim 5 wherein the first extender unit of the PKS catalyzes the conversion of 2-methyl-3-pentenoate N-acetylcysteamine thioester to the triketide (2R,3S, 4S,E)-2,4-dimethyl-3-hydroxy-5-heptenoic acid.

7. The method of claim 6, wherein when co-expressed in a host cell, the first and second extender units of the PKS catalyze the conversion of 2-methyl-3-pentenoate N-acetylcysteamine thioester to the tetraketide (5R,6S)-3,5-dimethyl-6-((S,E)-pent-3-en-2-yl)-dihydro-3H-pyran-2,4-dione.

8. The method of claim 5 wherein the first extender module has the structure: KS-AT-KR-ACP.

9. The method of claim 5 wherein the first extender unit is selected from the group consisting of module 2 of the erythromycin PKS (eryM2), module 5 of the erythromycin PKS (eryM5), module 6 of the erythromycin PKS (eryM6), module 3 of the geldanamycin PKS (gldM3), and module 1 of the soraphen PKS (sorM1).

10. The method of claim 5 wherein the second extender module has the structure: KS-AT-ACP.

11. The method of claim 5 wherein the second extender unit is selected from the group consisting of module 3 of the erythromycin PKS (eryM3), module 3 of the rapamycin PKS (rapM3), and module 6 of the pikromycin PKS (pikM6).

12. The method of claim 5, wherein the thioesterase domain is selected from the group consisting of eryTE and pikTE.

13. The method of claim 5, wherein the polyketide synthase has a structure is selected from the group consisting of eryM2-eryM3-eryTE, eryM5-eryM6-eryTE, and eryM6-eryM5-TE.

14. The method of claim 13, comprising growing the host cell in a medium comprising 2-methyl-3-pentenoate N-acetylcysteamine thioester under conditions wherein the cell converts 2-methyl-3-pentenoate N-acetylcysteamine thioester into (5R,6S)-3,5-dimethyl-6-((S,E)-pent-3-en-2-yl)-dihydro-3H-pyran-2,4-dione, and isolating the (5R,6S)-3,5-dimethyl-6-((S,E)-pent-3-en-2-yl)-dihydro-3H-pyran-2,4-dione.

15. The method of claim 14 further comprising converting the fermentation product (5R,6S)-3,5-dimethyl-6-((S,E)-pent-3-en-2-yl)-dihydro-3H-pyran-2,4-dione into (5R,6S)-3,3,5-trimethyl-6-((S,E)-pent-3-en-2-yl)-dihydro-3H-pyran-2,4-dione.

16. The method of claim 14, wherein the host cell is *Escherichia coli* or *Streptomyces coelicolor*.

17. An isolated compound of the formula:

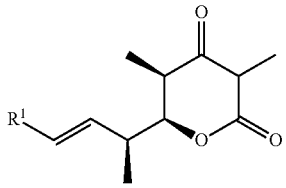

wherein $R^1$ is H, unsubstituted lower alkyl, or substituted lower alkyl.

18. An isolated compound of formula (I).

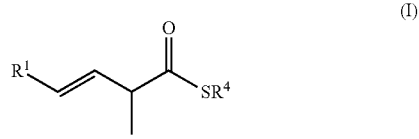

wherein $R^1$ is H, unsubstituted lower alkyl, or substituted lower alkyl; and $R^4$ is linear $C_1$-$C_{10}$ alkyl, or $CH_2CH_2NH(CO)R^5$, wherein $R^5$ is $C_1$-$C_{10}$ alkyl.

19. The compound of claim 18 that is 2-methyl-3-pentenoate N-acetylcysteamine thioester.

* * * * *